United States Patent
Kim et al.

(10) Patent No.: US 10,858,543 B2
(45) Date of Patent: Dec. 8, 2020

(54) ANTI-CORROSION POLISHING COMPOSITION

(71) Applicant: FUJIMI INCORPORATED, Aichi (JP)

(72) Inventors: Hooi-Sung Kim, Tualatin, OR (US); Anne Miller, Tualatin, OR (US)

(73) Assignee: FUJIMI INCORPORATED, Kiyosu (JP)

( * ) Notice: Subject to any disclaimer, the term of this patent is extended or adjusted under 35 U.S.C. 154(b) by 0 days.

(21) Appl. No.: 15/787,229

(22) Filed: Oct. 18, 2017

(65) Prior Publication Data

US 2019/0112504 A1    Apr. 18, 2019

(51) Int. Cl.
| | | |
|---|---|---|
| C09G 1/02 | (2006.01) | |
| C09K 15/06 | (2006.01) | |
| B24B 37/04 | (2012.01) | |
| C23F 3/00 | (2006.01) | |
| C07C 59/125 | (2006.01) | |
| C23F 3/04 | (2006.01) | |
| C23F 11/12 | (2006.01) | |
| C23F 11/10 | (2006.01) | |

(52) U.S. Cl.
CPC .............. C09G 1/02 (2013.01); B24B 37/044 (2013.01); C07C 59/125 (2013.01); C09K 15/06 (2013.01); C23F 3/00 (2013.01); C23F 3/04 (2013.01); C23F 11/10 (2013.01); C23F 11/128 (2013.01)

(58) Field of Classification Search
CPC ...... A61K 2800/30; A61K 8/34; A61K 8/365; A61K 8/368; A61K 8/9728; A61Q 15/00; C09G 1/02; C09G 1/06; B24B 37/044; C07C 59/125; C09D 1/02; C09K 15/06; C23F 3/00; C23F 11/10; C23F 11/128; C23F 3/04
USPC .... 252/79.1, 79.2, 79.3, 79.4; 438/692, 693, 438/694
See application file for complete search history.

(56) References Cited

U.S. PATENT DOCUMENTS

| | | | | |
|---|---|---|---|---|
| 4,830,783 A | * | 5/1989 | Ellis ..................... | C11D 3/0078 510/113 |
| 7,201,784 B2 | * | 4/2007 | Miller ..................... | C09G 1/02 106/3 |
| 7,699,897 B2 | * | 4/2010 | Nguyen .................. | A61K 8/31 132/202 |
| 2002/0095872 A1 | * | 7/2002 | Tsuchiya .................. | C09G 1/02 51/307 |

(Continued)

*Primary Examiner* — Lan Vinh
(74) *Attorney, Agent, or Firm* — Foley & Lardner LLP

(57) ABSTRACT

Provided herein are methods and compositions for chemical mechanical polishing (CMP) of metals. The present methods and compositions involve the use of a corrosion inhibitor having the general formula $C_mH_{2m+1}-(OCH_2CH_2)_n-L-R$ in the CMP slurry composition, where m is an integer between 6 and 11, inclusive of end points, and n is an integer greater than or equal to 6, L is a bond, —O—, —S—, —R$^1$—, —S—R$^1$—, or —O—R$^1$—, where R$^1$ is a $C_{1-4}$ alkylene; and R is an anionic group. The present methods and compositions can be used to achieve a high metal removal rate, while effectively inhibiting metal corrosion during CMP, and are particularly useful for CMP of cobalt (Co).

13 Claims, 4 Drawing Sheets

(56) References Cited

U.S. PATENT DOCUMENTS

2013/0210695 A1* 8/2013 Bjelopavlic .............. C11D 1/66
510/470

* cited by examiner

ANTI-CORROSION POLISHING COMPOSITION

TECHNICAL FIELD

The present technology generally relates to chemical mechanical polishing (CMP) of metal for microelectronic applications. The present technology relates to methods and slurry compositions that achieve a high metal removal rate, while exhibiting a great corrosion inhibition performance. The present methods and compositions are particularly useful in polishing cobalt (Co) and barrier films.

BACKGROUND

Cobalt (Co) is a relatively new polish material for the semiconductor industry. Cobalt has been used as a promising barrier material due to its lower resistivity compared to tantalum (Ta). More recently, cobalt has been also used as a contact material or metal gate fill due to its lower resistivity relative to tungsten (W).

Chemical mechanical polishing (CMP) is an important part of damascene process flow. The chemical compositions of CMP slurries are critical to the performance of the metal CMP process. The slurries generally comprise abrasive(s) which provide mechanical abrasion action in the metal polishing, as well as chemical agents that interact with metal film surface so that the polishing removal rate and corrosion rate can be controlled.

For metal bulk polish, it is preferred to have a very high metal removal rate (RR). Meanwhile, in order to obtain a planar polished surface, it is preferred that metal corrosion is inhibited or minimized. Typically, high pH slurries limit the metal removal rate (RR), and low pH slurries cause severe corrosion of the metal during CMP. Thus, there has been substantial effort in the field toward the development of slurry compositions at neutral or near-neutral pH, in order to achieve both high metal removal rate and good corrosion performance. Yet, conventional polishing slurries, even under neutral or near neutral pH conditions, still cause severe cobalt corrosion during CMP. Thus, there exists the need for the development of new slurry compositions, which enable high cobalt removal rate during CMP, while effectively inhibiting cobalt corrosion.

SUMMARY OF THE DISCLOSURE

Provided herein are methods and compositions for chemical mechanical polishing (CMP) of metals. In one aspect, provided herein are chemical mechanical polishing (CMP) compositions. In some embodiments, the CMP composition comprises at least one abrasive and at least one corrosion inhibitor, wherein the corrosion inhibitor comprises a compound represented by Formula (I):

where $6 \leq m \leq 20$;
$n \geq 5$,
L is a bond, —O—, —S—, —$R^1$—, —S—$R^1$—, or —O—$R^1$—, where $R^1$ is a $C_{1-4}$ alkylene; and R is an anionic group.

In some embodiments, the composition $n \geq 6$. In some embodiments, $5 \leq n \leq 12$. In some embodiments, $6 \leq m \leq 11$. In some embodiments, m=n=8.

In some embodiments, R is selected from carboxylic acid, sulphonic acid, phosphonic acid, and any salt thereof.

In some embodiments, the composition comprises a corrosion inhibitor that comprises capryleth-9 carboxylic acid having the structure of $CH_3(CH_2)_7(OCH_2CH_2)_8 OCH_2COOH$.

In some embodiments, the CMP composition comprises about 0.0001% to about 1% by weight of the corrosion inhibitor.

In some embodiments, the CMP composition comprises glycine or a salt thereof.

In some embodiments, the pH of the composition is in the range of about 6 to about 10, inclusive of the end points.

In some embodiments, the composition produces a cobalt static etching rate of about 20 Å/min or less at 50° C.

In some embodiments, the abrasive comprises silica particles or alumina particles.

In some embodiments, the CMP composition comprises
(a) about 0.01% to about 10% by weight of an abrasive;
(b) about 0.0001% to about 1% by weight of a corrosion inhibitor represented by Formula (I):

where $6 \leq m \leq 20$;
$n \geq 5$,
L is a bond, —O—, —S—, —$R^1$—, —S—$R^1$—, or —O—$R^1$—, where $R^1$ is a $C_{1-4}$ alkylene; and
R is an anionic group;
(c) about 0.1% to about 5% by weight of a complexing agent;
wherein the composition has a pH in the range of about 6 to about 10, inclusive of end points.

In some embodiments, the corrosion inhibitor is capryleth-9 carboxylic acid having the structure of $CH_3(CH_2)_7 (OCH_2CH_2)_8OCH_2COOH$.

In some embodiments, the complexing agent is glycine or a salt thereof.

In some embodiments, the CMP composition consists essentially of
(a) about 0.01% to about 10% by weight of an abrasive;
(b) about 0.0001% to about 1% by weight of capryleth-9 carboxylic acid having the structure of $CH_3(CH_2)_7 (OCH_2CH_2)_8OCH_2COOH$;
(c) about 0.1% to about 5% by weight of glycine or a salt thereof.
wherein the composition has a pH in the range of about 6 to about 10, inclusive of end points.

In some embodiments, the CMP composition consists of
(a) about 0.01% to about 10% by weight of an abrasive;
(b) about 0.0001% to about 1% by weight of capryleth-9 carboxylic acid having the structure of $CH_3(CH_2)_7 (OCH_2CH_2)_8OCH_2COOH$;
(c) about 0.1% to about 5% by weight of glycine or a salt thereof;
(d) a pH adjusting agent; wherein the composition has a pH in the range of about 6 to about 10, inclusive of end points; and
(e) optionally an oxidizer.

In some embodiments, the CMP composition comprises
(a) about 0.01% to about 10% by weight of an abrasive;
(b) a corrosion inhibitor consisting of about 0.0001% to about 1% by weight of capryleth-9 carboxylic acid having the structure of $CH_3(CH_2)_7(OCH_2CH_2)_8OCH_2COOH$;
(c) about 0.1% to about 5% by weight of glycine or a salt thereof;
wherein the composition has a pH in the range of about 6 to about 10, inclusive of end points.

In a second aspect, provided herein are methods for chemical mechanical polishing (CMP) of an object having at least one metal surface. In some embodiments, the method comprises:

contacting the metal surface with a polishing pad;
delivering a polishing slurry to the metal surface,
wherein the polishing slurry comprises at least one abrasive and at least one corrosion inhibitor;
wherein the corrosion inhibitor comprises a compound represented by Formula (I):

$$C_mH_{2m+1}-(OCH_2CH_2)_n\text{-L-R} \qquad (I)$$

where $6 \leq m \leq 20$;
$n \geq 5$,
L is a bond, —O—, —S—, —$R^1$—, —S—$R^1$—, or —O—$R^1$—, where $R^1$ is a $C_{1-4}$ alkylene; and
R is an anionic group; and
polishing the metal surface with the polishing slurry.

In a third aspect, provided herein are methods for preventing metal corrosion during chemical mechanical polishing (CMP). In some embodiments, the method comprises:

using for the CMP a slurry comprising at least one corrosion inhibitor represented by Formula (I):

$$C_mH_{2m+1}-(OCH_2CH_2)_n\text{-L-R} \qquad (I)$$

where $6 \leq m \leq 20$;
$n \geq 5$,
L is a bond, —O—, —S—, —$R^1$—, —S—$R^1$—, or —O—$R^1$—, where $R^1$ is a $C_{1-4}$ alkylene; and
R is an anionic group.

In some embodiments of the present method, the corrosion inhibitor is capryleth-9 carboxylic acid having the structure of $CH_3(CH_2)_7(OCH_2CH_2)_8OCH_2COOH$.

In some embodiments, the metal is cobalt (Co).

In some embodiments, method is capable of achieving at least Grade 3 corrosion grade at a Co removal rate of greater than 2000 Å/min.

In some embodiments, the method produces a polished surface devoid of corrosion visible to the naked eye.

In some embodiments, the method produces a polished surface comprising total corrosion area observable under 10× magnification of a microscope of less than 1% of the total area of the polished surface.

In a fourth aspect, provided herein are systems for chemical mechanical polishing (CMP). In some embodiments, the system comprises a substrate comprising at least one metal surface; a polishing pad, and a polishing slurry, wherein the polishing slurry comprises at least one abrasive and at least one corrosion inhibitor; and
wherein the corrosion inhibitor comprises a compound represented by Formula (I):

$$C_mH_{2m+1}-(OCH_2CH_2)_n\text{-L-R} \qquad (I)$$

where $6 \leq m \leq 20$;
$n \geq 5$,
L is a bond, —O—, —S—, —$R^1$—, —S—$R^1$—, or —O—$R^1$—, where $R^1$ is a $C_{1-4}$ alkylene; and
R is an anionic group.

In a fifth aspect, provided herein are substrates. In some embodiments, the substrate comprises at least one metal surface, wherein the substrate is in contact with a chemical mechanical polishing (CMP) slurry, and wherein the CMP slurry comprises at least one corrosion inhibitor represented by Formula (I):

$$C_mH_{2m+1}-(OCH_2CH_2)_n\text{-L-R} \qquad (I)$$

where $6 \leq m \leq 11$;
$n \geq 6$,
L is a bond, —O—, —S—, —$R^1$—, —S—$R^1$—, or —O—$R^1$—, where $R^1$ is a $C_{1-4}$ alkylene; and
R is an anionic group.

In some embodiments of the substrates, the metal surface comprises cobalt.

In some embodiments of the substrates, the metal surface is devoid of corrosion visible to the naked eye.

In some embodiments of the substrates, the metal surface comprises total corrosion area observable under 10× magnification of a microscope of less than 1% of the total area of the metal surface.

DETAILED DESCRIPTION

Figure 1:
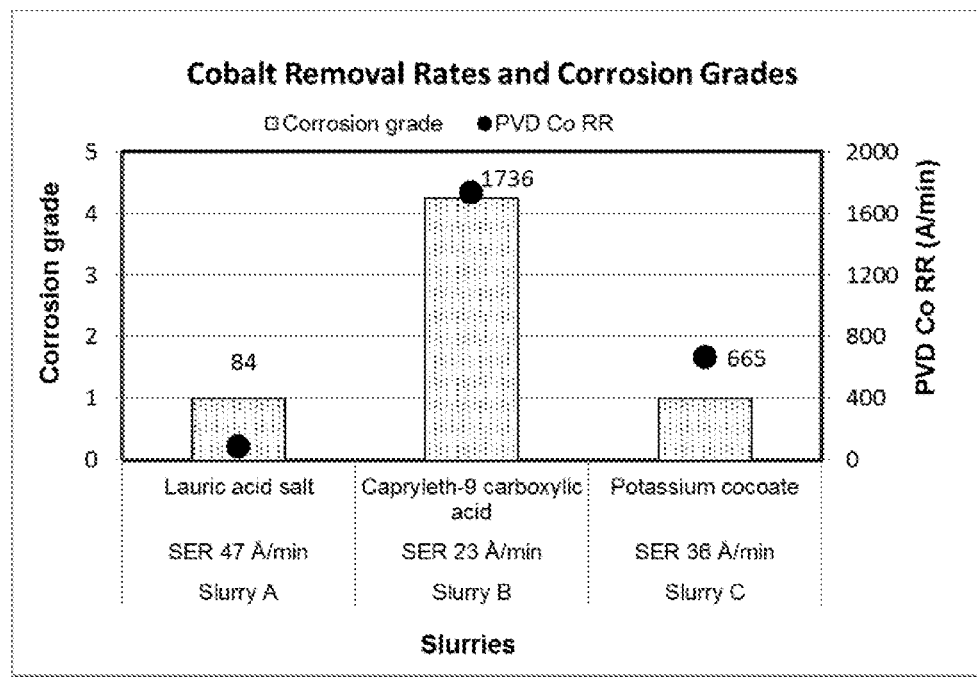
FIG. 1 shows the cobalt corrosion grade and removal rate of three candidate slurry compositions. Each composition contains a candidate corrosion inhibitor at the concentration of 1 mM. The corrosion grades were evaluated after static etching tests at 50° C. for 3 minutes.

Provided herein are compositions and related methods and systems for performing chemical mechanical polishing (CMP) of a surface. As used herein, the term "chemical mechanical polishing" or "planarization" refers to a process of planarizing (polishing) a surface with the combination of surface chemical reaction and mechanical abrasion. In some embodiments, the chemical reaction is initiated by applying to the surface a composition (interchangeably referred to as a 'polishing slurry,' a 'polishing composition,' a 'slurry composition' or simply a slurry') capable of reacting with a surface material, thereby turning the surface material into a product that can be more easily removed by simultaneous mechanical abrasion. In some embodiments, the mechanical abrasion is performed by contacting a polishing pad with the surface, and moving the polishing pad relative to the surface.

Composition

A polishing slurry composition may comprise an aqueous solvent and at least one Co corrosion inhibitor. The term "aqueous solvent" as used herein refers to water, or a solvent mixture of water (>50%) and a water miscible solvent (<50%). A polishing slurry may contain chemical ingredients selected specifically for processing a certain type of surface, such as for polishing a cobalt-containing surface as opposed to a different surface that does not contain a metal. Examples of such chemical ingredients include catalysts, stabilizers, inhibitors, surfactants, oxidants, and others. Each of these ingredients may be selected to improve desired processing, for example efficient removal, of a material from the surface. Additionally, the slurry composition may also contain abrasive particles or grains to enhance the removal rate by mechanical abrasion in the presence of the slurry. The type of abrasive particles may also be selected based on the type of substrate being processed.

Chemical mechanical polishing (CMP) is an important part of damascene process flow. In some embodiments, a metal material is removed in a single step that uncovers a dielectric surface. In other embodiments, a "two-step" process can be used. In a first step, a large portion of the excess metal is removed but the dielectric layer is not exposed. This step is commonly referred to as a "bulk" removal step during which a high metal removal rate is desired for high throughput. A subsequent (second) step can be used to remove the remaining metal and expose the underlying dielectric and metal surface. This step is sometimes referred to as a "polishing" step, wherein a high metal removal rate may be important, when balanced with other also important performance requirements, such as the tendency of some CMP slurries to cause strong corrosion of the metal surface.

Corrosion Inhibitor

Corrosion is a common side-effect of a polishing slurry. During the CMP process, chemical ingredients of the polishing slurry that remain on the metal surface continue to etch the metal, beyond the effects of the CMP. High level of corrosion may contribute to surface defects such as pitting and keyholing. These defects may significantly impair the properties and hamper the usefulness of final products manufactured out of the polished products. In some embodiments, corrosion is measured by visually inspecting a polished surface, with or without a microscope, and determining the percentage of a surface area of interest that has been affected by corrosion during the CMP process (See Example 1).

In some embodiments, the present polishing slurry is suitable for cobalt (Co) removal. In some embodiments, a high Co removal rate is desired. In some embodiments, a high removal rate is also balanced with the need to prevent a high level of Co corrosion under the harsh conditions under which CMP is performed. In some embodiments, these goals are achieved by performing Co CMP using a polishing slurry that contains a suitable Co corrosion inhibitor, which on one hand effectively suppresses Co corrosion under the CMP conditions, and on the other hand also permits a high Co removal rate.

In some embodiments, the Co removal rate of a CMP procedure using the present polishing slurry is less than 500 Å/min, or less than 1000 Å/min, or less than 1500 Å/min, or less than 2000 Å/min, or less than 2500 Å/min, or less than 3000 Å/min, or less than 3500 Å/min, or less than 4000 Å/min, or less than 4500 Å/min or less than 5000 Å/min.

A static etch rate (SER) of a slurry composition can be measured as the rate at which a target metal statically dissolves in a slurry composition without the aid of mechanical abrasion. Thus statistic etch rate can be indicative of surface protection provided by a corrosion inhibitor contained in the slurry composition. In some embodiments, the corrosion inhibitor functions to maintain a high metal removal rate while keeping the static etch rate low at the same time. In some embodiments, a cobalt coupon is immersed in the slurry composition at 50° C. for 3 minutes, then the static etch rate is measured as the reduction in the coupon's thickness per unit time. In some embodiments, the static etch rate of the present slurry composition is in the range of about 0 to 5 angstrom per minute (Å/min). In some embodiments, the static etch rate of a slurry composition is preferably in the range of about 5 to about 10 Å/min. In some embodiments, the static etch rate of a slurry composition is preferably in the range of about 10 to about 20 Å/min. In some embodiments, the static etch rate of a slurry composition is preferably in the range of about 20 to about 30 Å/min. In some embodiments, the static etch rate of a slurry composition is preferably in the range of about 30 to about 40 Å/min. In some embodiments, the static etch rate of a slurry composition is preferably in the range of about 40 to about 50 Å/min.

Without being bound by the theory, it is contemplated that a suitable corrosion inhibitor compound according to the present disclosure comprises at least one reactive group capable of associating with the metal surface, and at least one hydrophobic group. The hydrophobic groups of the inhibitor molecules may align with one another, such that the inhibitor molecules form an impervious film covering the metal surface, thereby providing the protection against corrosion caused by the slurry chemistry. In some embodiments, the attachment of the reactive group to the metal surface is achieved through the formation of chemical or physical binding between the reactive group and a metal oxidation product formed on the metal surface, such as Co oxide or Co hydroxide on a Co surface.

In some embodiments, the reactive group of the corrosion inhibitor is an anionic group. The term "anionic group" as used herein refers to a chemical moiety that is negatively charged or is capable of supporting a negative charge at the neutral pH or the pH of the environment that the moiety is exposed to. Anionic groups include but are not limited to carboxylic acid, sulphonic acid, phosphonic acid, and salts thereof, such as carboxylates, sulphonates, sulphates, and phosphonates.

In some embodiments, the hydrophobic group of the corrosion inhibitor is an alkyl group. In some embodiments, the alkyl group is saturated, non-substituted and non-branched. In some embodiments, the alkyl group is unsaturated. In some embodiments, the alkyl group is substituted. In some embodiments, the alkyl group is branched. In some embodiments, the alkyl group comprises between 4 and 15 carbon atoms, inclusive of the end points. In some embodiments, the alkyl group comprises between 6 and 11 carbon atoms, inclusive of the end points. In some embodiments, the alkyl group comprises between 8 and 10 carbon atoms, inclusive of the end points. In some embodiments, the alkyl group comprises about 4, 5, 6, 7, 8, 9, 10, 11, 12, 13, 14, 15 carbon atoms. In some embodiments, the alkyl group is $CH_3-(CH_2)_7-$.

In some embodiments, the reactive group and the hydrophobic group of the corrosion inhibitor are separated by a hydrophilic chain. In some embodiments, the hydrophilic chain comprises multiple ethylene oxide repeating units, each unit having the structure $-(O-CH_2-CH_2)-$. In some embodiments, the hydrophobic chain comprises 6 or more ethylene oxide repeating units. In some embodiments, the hydrophobic chain comprises about 6 to about 12 ethylene oxide repeating units. In some embodiments, the hydrophobic chain comprises about 8 to about 10 ethylene oxide repeating units. In some embodiments, the hydrophobic chain comprises about, 6, 7, 8, 9, 10, 11, or 12 ethylene oxide repeating units.

In some embodiments, the corrosion inhibitor is represented by Formula (I):

$$C_mH_{2m+1}-(OCH_2CH_2)_n-L-R \qquad (I)$$

where m is an integer between 6 and 20, inclusive of the end points;

n is an integer greater than or equal to 5;

L is a bond, $-O-$, $-S-$, $-R^1-$, $-S-R^1-$, or $-O-R^1-$, where $R^1$ is a $C_{1-4}$ alkylene; and R is an anionic group.

In some embodiments, the corrosion inhibitor is represented by above Formula (I), where m is an integer between 6 and 11, inclusive of end points. In some embodiments, the corrosion inhibitor is represented by above Formula (I), where m is an integer between 7 and 10, inclusive of end points; or m is 8; or m is 9.

In some embodiments, the corrosion inhibitor is represented by above Formula (I), where m is an integer between 7 and 19, inclusive of end points; or m is an integer between 8 and 18, inclusive of end points; or m is an integer between 9 and 17, inclusive of end points; or m is an integer between 10 and 16, inclusive of end points; or m is an integer between 11 and 15, inclusive of end points; or m is an integer between 12 and 14, inclusive of end points; or m is 13.

In some embodiments, the corrosion inhibitor is represented by above Formula (I), where m is less than 20, or m is less than 19, or m is less than 18, or m is less than 17, or m is less than 16, or m is less than 15, or m is less than 14, or m is less than 13, or m is less than 12, or m is less than 11, or m is less than 10, or m is less than 9, or m is less than 8, or m is less than 7, or m is less than 6.

In some embodiments, the corrosion inhibitor is represented by above Formula (I), where m is an integer between 6 and 11, inclusive of end points; and where n is an integer greater than or equal to 5.

In some embodiments, the corrosion inhibitor is represented by above Formula (I), where m is an integer between 7 and 10, inclusive of end points, or m is 8, or m is 9; and where n is an integer greater than or equal to 5.

In some embodiments, the corrosion inhibitor is represented by above Formula (I), where m is an integer between 7 and 19, inclusive of end points, or m is an integer between 8 and 18, inclusive of end points, or m is an integer between 9 and 17, inclusive of end points, or m is an integer between 10 and 16, inclusive of end points, or m is an integer between 11 and 15, inclusive of end points, or m is an integer between 12 and 14, inclusive of end points, or m is 13; and where n is an integer greater than or equal to 5.

In some embodiments, the corrosion inhibitor is represented by above Formula (I), where m is less than 20, or m is less than 19, or m is less than 18, or m is less than 17, or m is less than 16, or m is less than 15, or m is less than 14, or m is less than 13, or m is less than 12, or m is less than 11, or m is less than 10, or m is less than 9, or m is less than 8, or m is less than 7, or m is less than 6; and where n is an integer greater than or equal to 5.

In some embodiments, the corrosion inhibitor is represented by above Formula (I), where n is an integer between 5 and 12, inclusive of end points, or n is an integer between 6 and 11, inclusive of end points; or n is an integer between 7 and 10, inclusive of end points, or n is 8, or n is 9.

In some embodiments, the corrosion inhibitor is represented by above Formula (I), where n is an integer greater than or equal to 5, or n is an integer greater than or equal to 6, or n is an integer greater than or equal to 7, or n is an integer greater than or equal to 8, or n is an integer greater than or equal to 9, or n is an integer greater than or equal to 10, or n is an integer greater than or equal to 11.

In some embodiments, the corrosion inhibitor is represented by above Formula (I), where n is an integer between 5 and 12, inclusive of end points, or n is an integer between 6 and 11, inclusive of end points, or n is an integer between 7 and 10, inclusive of end points, or n is 8, or n is 9; and where m is an integer between 6 and 20, inclusive of the end points.

In some embodiments, the corrosion inhibitor is represented by above Formula (I), where n is an integer greater than or equal to 5, or n is an integer greater than or equal to 6, or n is an integer greater than or equal to 7, or n is an integer greater than or equal to 8, or n is an integer greater than or equal to 9, or n is an integer greater than or equal to 10, or n is an integer greater than or equal to 11; and where m is an integer between 6 and 20, inclusive of the end points.

In some embodiments, the corrosion inhibitor is represented by above Formula (I), where m=n=8.

In some embodiments, the corrosion inhibitor is represented by above Formula (I), where m=n=8, and R is —COOH.

In some embodiments, the corrosion inhibitor is represented by above Formula (I), where $R^1$ is a $C_{1-4}$ alkylene, or $R^1$ is a $C_{1-3}$ alkylene, or $R^1$ is a $C_1$ alkylene, or $R^1$ is a $C_2$ alkylene. In some embodiments, L is —O—$CH_2$—.

In some embodiments, the corrosion inhibitor is represented by above Formula (I), where R is selected from carboxylic acid, sulphonic acid, phosphonic acid, and salts thereof. In some embodiments, R is —(C(=O)OH).

In some embodiments, the corrosion inhibitor is represented by above Formula (I), where $R^1$ is a $C_{1-4}$ alkylene, or $R^1$ is a $C_{1-3}$ alkylene, or $R^1$ is a $C_1$ alkylene, or $R^1$ is a $C_2$ alkylene, and where R is selected from carboxylic acid, sulphonic acid, phosphonic acid, and salts thereof.

In some embodiments, the corrosion inhibitor is represented by above Formula (I), where L is —O—$CH_2$—, and R is —(C(=O)OH).

In some embodiments, the corrosion inhibitor is caprylethl-9 carboxylic acid having the structure of $CH_3(CH_2)_7(OCH_2CH_2)_8OCH_2COOH$.

In some embodiments, the present slurry composition comprises about 0.0001% to about 1% by weight of the corrosion inhibitor. In some embodiments, the present slurry composition comprises above about 0.01 wt % of the corrosion inhibitor. In some embodiments, the present slurry composition comprises above about 0.02 wt % of the corrosion inhibitor. In some embodiments, the present slurry composition comprises above about 0.03 wt % of the corrosion inhibitor. In some embodiments, the present slurry composition comprises above about 0.04 wt % of the corrosion inhibitor. In some embodiments, the present slurry composition comprises above about 0.05 wt % of the corrosion inhibitor. In some embodiments, the present slurry composition comprises above about 0.06 wt % of the corrosion inhibitor. In some embodiments, the present slurry composition comprises above about 0.07 wt % of the corrosion inhibitor. In some embodiments, the present slurry composition comprises above about 0.08 wt % of the corrosion inhibitor. In some embodiments, the present slurry composition comprises above about 0.09 wt % of the corrosion inhibitor. In some embodiments, the present slurry composition comprises above about 0.1 wt % of the corrosion inhibitor. In some embodiments, the present slurry composition comprises above about 0.15 wt % of the corrosion inhibitor. In some embodiments, the present slurry composition comprises above about 0.2 wt % of the corrosion inhibitor. In some embodiments, the present slurry composition comprises above about 0.25 wt % of the corrosion inhibitor. In some embodiments, the present slurry composition comprises above about 0.3 wt % of the corrosion inhibitor. In some embodiments, the present slurry composition comprises above about 0.35 wt % of the corrosion inhibitor. In some embodiments, the present slurry composition comprises above about 0.4 wt % of the corrosion inhibitor. In some embodiments, the present slurry composition comprises above about 0.45 wt % of the corrosion inhibitor. In some embodiments, the present slurry composition comprises above about 0.5 wt % of the corrosion inhibitor. In some embodiments, the present slurry composition comprises above about 0.6 wt % of the corrosion inhibitor. In some embodiments, the present slurry composition comprises above about 0.7 wt % of the corrosion inhibitor. In some embodiments, the present slurry composition comprises above about 0.8 wt % of the corrosion inhibitor. In some embodiments, the present slurry composition comprises above about 0.9 wt % of the corrosion inhibitor. In some embodiments, the present slurry composition comprises above about 1.0 wt % of the corrosion inhibitor.

Complexing Agent

In some embodiments, the present slurry composition further comprises at least one complexing agent. As used herein, the term "complexing agent" refers to a chemical compound that interacts with surfaces of metals to be polished during the CMP process. In some embodiments, the complexing agent is a nitrogen (N—) containing compound. Particularly, in some embodiments, the complexing agent comprises at least one amino group.

"Amino groups" as used herein refer to functional groups that contain a basic nitrogen atom having a lone pair and single bonds to hydrogen atom(s) and/or substituent chemical group(s). The substituent chemical group is not specifically limited, and in various embodiments, can be either an organic or inorganic group, such as a halogen group, an alkyl group, an aromatic group or an acyl group. Amines are compounds containing at least one amino group. Particularly, primary amines refer to nitrogen-containing compounds having two hydrogen atoms and one substituent group covalently bonded to the nitrogen. Secondary amines refer to nitrogen-containing compounds having one hydrogen atom and two substituent groups covalently bonded to the nitrogen. Tertiary amines are nitrogen-containing compounds where the nitrogen atom covalently bonded to three substituent groups. Cyclic amines are either secondary or tertiary amines where the nitrogen atom is included in a cyclic structure formed by the substituent groups. Most amino acids are primary amines. Proline is a secondary cyclic amine.

In some embodiments, the complexing agent further comprises at least one carboxyl group having the general formula —(C(=O)OH). In some embodiments, the carboxyl group serves to enhance chemical interaction between the complexing agent and the metal to be polished, for example by adsorbing the complexing agent onto the surface of the metal film.

In some embodiments, the complexing agent has at least one amino group and at least one carboxyl group connected by a chemical linking structure. The chemical linking between the carboxyl group and the amino group of the complexing agent is not specifically limited. In some embodiments, the chemical linking structure between the carboxyl group and the amino group of the complexing agent can be a linear, branched and/or cyclic carbon chain having 1 to 20 carbon atoms. Optionally, the chemical linking structure comprises unsaturated covalent bonds and heteroatoms, such as nitrogen, oxygen, sulfur, phosphate, and/or halogens. Optionally, the carbon chain comprises one or more substituted or unsubstituted aryls, acyls, esters, alkoxyls, alkyls, carbonyls, hydroxyls, etc.

In some embodiments, the complexing agent has a cyclic structure. According to the present disclosure, the cyclic structure may be an aromatic ring or an aliphatic ring. In some embodiments, the cyclic structure may contain a heteroatom. In some embodiments, the cyclic structure may be a condensed ring containing two or more rings. In some embodiments, the heteroatom referred herein may be selected from the group consisting of a nitrogen atom, an oxygen atom, a sulfur atom, and a phosphorus atom. In various embodiments, the cyclic structure may be branched or unbranched, saturated or unsaturated. The cyclic structure may have 3 to 12 ring members, particularly, 4 to 7 ring members, and more particularly 5 to 6 ring members. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cyclopentane ring, a cycloheptatriene ring, a cycloheptadiene ring, a cycloheptene ring, and a cycloheptane ring.

In some embodiments, the complexing agent is an amino acid or analog thereof. The amino acid complexing agents of the present disclosure include but are not limited to α-amino acids, where the amino group is attached to the α-carbon in the carbon backbone connecting the amino group and carboxyl group. For example, in various embodiments, the amino acid complexing agent can be β-, γ-, δ-amino acids, etc. The amino acid complexing agents of the present disclosure include but are not limited to the 20 natural amino acids and derivatives or analogs thereof. In some embodiments, the complexing agent is glycine or salts thereof.

As used herein, analogs of amino acid include, but are not limited to, amino acid isosteres. In some embodiments, the amino acid isostere comprises a carboxylic acid isostere, an amine isostere, or a combination thereof. In some embodiments, the carboxylic acid group of the amino acid is replaced with carboxylic acid isostere. Non-limiting examples of carboxylic acid isosteres include sulfonic acids, sulfinic acids, hydroxamic acids, hydroxamic esters, phosphonic acids, phosphinic acids, sulfonamides, acylsulfonamides, sulfonylureas, acylureas, tetrazole, thiazolidinediones, oxazolidinediones, oxadiazol-5(4H)-ones, thiadiazol-5(4H)-ones, oxathidiazole-5(4H)-ones, isoxazoles, tetramic acids, or cyclopentane-1,3-diones. In some embodiments, the amino group of the amino acid is replaced with an amine isostere. Non-limiting examples of amine isosteres include hydroxyl and thiol.

In some embodiments, the present slurry composition comprises about 0.1% to about 5% by weight of the complexing agent. In some embodiments, the present slurry composition comprises about 0.1% to about 5% by weight of the complexing agent. In some embodiments, the present slurry composition comprises about 0.1% by weight of the complexing agent. In some embodiments, the present slurry composition comprises about 0.2% by weight of the complexing agent. In some embodiments, the present slurry composition comprises about 0.3% by weight of the complexing agent. In some embodiments, the present slurry composition comprises about 0.4% by weight of the complexing agent. In some embodiments, the present slurry composition comprises about 0.5% by weight of the complexing agent. In some embodiments, the present slurry composition comprises about 0.6% by weight of the complexing agent. In some embodiments, the present slurry composition comprises about 0.7% by weight of the complexing agent. In some embodiments, the present slurry composition comprises about 0.8% by weight of the complexing agent. In some embodiments, the present slurry composition comprises about 0.9% by weight of the complexing agent. In some embodiments, the present slurry composition comprises about 1% by weight of the complexing agent. In some embodiments, the present slurry composition comprises about 2% by weight of the complexing agent. In some embodiments, the present slurry composition comprises about 3% by weight of the complexing agent. In some embodiments, the present slurry composition comprises about 4% by weight of the complexing agent. In some embodiments, the present slurry composition comprises about 5% by weight of the complexing agent.

pH Adjusting Agent

In some embodiments, the present slurry composition further comprises at least one pH adjusting agent. In some embodiments, the pH of the present slurry composition is, although not particularly limited, in the range of about 1 to about 13, inclusive of the end points. In some embodiments, the pH of the present slurry composition is in the range of about 1.5 to about 12.5, inclusive of the end points. In some embodiments, the pH of the present slurry composition is in the range of about 2 to about 12, inclusive of the end points. In some embodiments, the pH of the present slurry composition is in the range of about 2.5 to about 11.5, inclusive of the end points. In some embodiments, the pH of the present slurry composition is in the range of about 3 to about 11, inclusive of the end points. In some embodiments, the pH of the present slurry composition is in the range of about 3.5 to about 10.5, inclusive of the end points. In some embodiments, the pH of the present slurry composition is in the range of about 4 to about 10, inclusive of the end points. In some embodiments, the pH of the present slurry composition is in the range of about 4.5 to about 9.5, inclusive of the end points. In some embodiments, the pH of the present slurry composition is in the range of about 5 to about 9, inclusive of the end points. In some embodiments, the pH of the present slurry composition is in the range of about 5.5 to about 8.5, inclusive of the end points. In some embodiments, the pH of the present slurry composition is in the range of about 6 to about 8, inclusive of the end points. In some embodiments, the pH of the present slurry composition is about 7. In some embodiments, the pH of the present slurry composition is about 7.5.

In some embodiments, the pH of the present slurry composition is in the range of about 6 to about 9, inclusive of the end points. In some embodiments, the pH of the present slurry composition is in the range of about 6 to about 10, inclusive of the end points. In some embodiments, the pH of the present slurry composition is in the range of about 6 to about 11, inclusive of the end points. In some embodiments, the pH of the present slurry composition is in the range of about 6 to about 12, inclusive of the end points.

In some embodiments, an acid or an alkali is used as the pH adjusting agent. The acid or alkali used in connection with the present invention can be organic or inorganic compounds. Examples of the acid include inorganic acids such as sulfuric acid, nitric acid, boric acid, carbonic acid, hypophosphorous acid, phosphorous acid, and phosphoric acid; and organic acids such as carboxylic acids including formic acid, acetic acid, propionic acid, butyric acid, valeric acid, 2-methylbutyric acid, n-hexanoic acid, 3,3-dimethylbutyric acid, 2-ethylbutyric acid, 4-methylpentanoic acid, n-heptanoic acid, 2-methylhexanoic acid, n-octanoic acid, 2-ethylhexanoic acid, benzoic acid, glycolic acid, salicylic acid, glyceric acid, oxalic acid, malonic acid, succinic acid, glutaric acid, adipic acid, pimelic acid, maleic acid, phthalic acid, malic acid, tartaric acid, citric acid, and lactic acid, and organic sulfuric acids including methanesulfonic acid, ethanesulfonic acid, and isethionic acid. Examples of the alkali include hydroxides of an alkali metal, such as potassium hydroxide; ammonium hydroxide, ethylene diamine, and piperazine; and quaternary ammonium salts such as tetramethyl ammonium hydroxide and tetraethyl ammonium hydroxide. These acids or alkalis can be used either singly or in combination of two or more types.

Content of the acid or alkali in the slurry composition is not particularly limited as long as it is an amount allowing the polishing composition to be within the aforementioned pH range.

Abrasive

In some embodiments, the present slurry composition further comprises at least one abrasive. The abrasive in the polishing slurry provides or enhances mechanical abrasion effects during the CMP process. Examples of abrasives that can be used in connection with the present disclosure include but are not limited to alumina abrasive, silica abrasive, ceria abrasive, titanium oxide, zirconia, or mixtures thereof. The preferred abrasives are alumina and silica. In order to reduce scratch defects, the mean particle size of the abrasive is preferably controlled. In some embodiments, the particle size profile of the abrasive is measured by D90, which is a characteristic number given by a particle sizing instrument to indicate that the sizes of 90% of particles are less than the characteristic number. In some embodiments, the mean particle size is less than 0.3 micron and the D90 of the abrasive is less than 1 micron. Particularly, in some embodiments, the mean particle size is in between 0.01 and 0.30 micron and D90 is less than 0.5 micron.

In some embodiments, the present slurry composition comprises about 0.01% to about 10% by weight of the abrasive. In some embodiments, the present slurry composition comprises less than 10% by weight of the abrasive. In some embodiments, the present slurry composition comprises less than 9% by weight of the abrasive. In some embodiments, the present slurry composition comprises less than 8% by weight of the abrasive. In some embodiments, the present slurry composition comprises less than 7% by weight of the abrasive. In some embodiments, the present slurry composition comprises less than 6% by weight of the abrasive. In some embodiments, the present slurry composition comprises less than 5% by weight of the abrasive. In some embodiments, the present slurry composition comprises less than 4% by weight of the abrasive. In some embodiments, the present slurry composition comprises less than 3% by weight of the abrasive. In some embodiments, the present slurry composition comprises less than 2% by weight of the abrasive. In some embodiments, the present slurry composition comprises less than 1% by weight of the abrasive. In some embodiments, the present slurry composition comprises less than 0.5% by weight of the abrasive. In some embodiments, the present slurry composition comprises less than 0.2% by weight of the abrasive.

Other Component

The slurry composition of the present invention may contain, if necessary, other components, such as a preservative, a biocide, an oxidizing agent, a reducing agent, a polymer, a surfactant, or the like.

An oxidizing agent may be added to the present slurry composition to oxidize a metal surface of a polishing object, thereby enhancing the metal removal rate of the CMP process. In some embodiments, an oxidizing agent is added to the slurry composition only prior to use. In other embodiments, an oxidizing agent is mixed with other ingredients of the slurry composition at approximately the same time during a manufacturing procedure. In some embodiments, the present composition is manufactured and sold as stock compositions, and an end customer can choose to dilute the stock composition as needed and/or add a suitable amount of an oxidizing agent before using.

Examples of the oxidizing agent which may be used include but are not limited to hydrogen peroxide, sodium peroxide, barium peroxide, an organic oxidizing agent, ozone water, a silver (II) salt, an iron (III) salt, permanganese acid, chromic acid, dichromic acid, peroxodisulfuric acid, peroxophosphoric acid, peroxosulfuric acid, peroxoboric acid, performic acid, peracetic acid, perbenzoic acid, perphthalic acid, hypochlorous acid, hypobromous acid, hypoiodous acid, chloric acid, chlorous acid, perchloric acid, bromic acid, iodic acid, periodic acid, persulfuric acid, dichloroisocyanuric acid, and a salt thereof. The oxidizing agent may be used either singly or as a mixture of two or more kinds. Among them, hydrogen peroxide, ammonium persulfate, periodic acid, hypochlorous acid, and sodium dichloroisocyanurate are preferable.

Suitable content of the oxidizing agent can be determined based on particular needs. For example, the metal removal rate may be expected to increase as the concentration of the oxidizing agent increases. In some embodiments, content of the oxidizing agent in the polishing composition is 0.1 g/L or more. In some embodiments, content of the oxidizing agent in the polishing composition is 1 g/L or more. In some embodiments, content of the oxidizing agent in the polishing composition is 3 g/L or more.

In some embodiments, content of the oxidizing agent in the polishing composition is 200 g/L or less. In some embodiments, content of the oxidizing agent in the polishing composition is 100 g/L or less. In some embodiments, content of the oxidizing agent in the polishing composition is 40 g/L or less. As the content of the oxidizing agent decreases, the cost involved with materials of the polishing composition can be saved and a load involved with treatment of the polishing composition after polishing use, that is, a load involved with waste treatment, can be reduced. It is also possible to reduce the possibility of excessive oxidation of a surface by reducing the content of an oxidizing agent.

In some embodiments, for the purpose of enhancing the hydrophilicity of the surface to be polished or increasing the dispersion stability of abrasive, a water soluble polymer may be added to the present slurry composition. Examples of the water soluble polymer include a cellulose derivative such as hydroxymethyl cellulose, hydroxyethyl cellulose (HEC), hydroxypropyl cellulose, hydroxyethylmethyl cellulose, hydroxypropylmethyl cellulose, methyl cellulose, ethyl cellulose, ethylhydroxyethyl cellulose, or carboxymethyl cellulose; an imine derivative such as poly(N-acylalkyleneimine); polyvinyl alcohol; modified (cation modified or non-ion modified) polyvinyl alcohol; polyvinyl pyrrolidone; polyvinylcaprolactam; polyoxyalkylene such as polyoxyethylene; and a copolymer containing those constitutional units. The water soluble polymer may be used either alone or as a mixture of two or more kinds.

In some embodiments, the slurry composition according to the present disclosure also comprises at least one surfactant. Without being bound by the theory, it is contemplated that surfactants can improve surface smoothness of polished metal film and reduce defects. Surfactants can also improve the within-wafer uniformity of removal rate. Non-ionic, anionic, cationic, and Zwitterionic surfactants can all be used. Exemplary surfactants that can be used in connection with the present disclosure include but are not limited to polyethylene glycol sorbitan monolaurate and other polyoxyethylene derivatives of sorbitan esters under trade name "Tween" from Uniqema; polyethylene glycol octadecyl ether and other polyoxyethylene fatty ether under trade name "Brij" from Uniqema; nonylphenol ethoxylates under trade name Tergitol from Dow Chemical; octylphenol ethoxylates under trade name Triton X from Dow Chemical; sodium lauryl sulfate and other surfactants of salts of alkyl sulfate; sodium 1-dodecanesulfonate and other surfactants of salts of alkyl sulfonate; quarternary ammonium salts. The surfactant concentration presented in the CMP slurry of this disclosure can be in a range from 0 to 1% by weight and preferably from 0.01 to 0.2% by weigh. These surfactants may be used either alone or in mixture of two or more kinds thereof.

In some embodiments, the slurry composition according to the present disclosure may also comprise a biocide or other preservatives. Examples of preservatives and biocides that may be used in connection with the present invention include an isothiazoline-based preservative such as 2-methyl-4-isothiazolin-3-one or 5-chloro-2-methyl-4-isothiazolin-3-one, paraoxybenzoate esters, and phenoxyethanol, and the like. These preservatives and biocides may be used either alone or in mixture of two or more kinds thereof.

Methods and Compositions

In another aspect of the present disclosure, provided herein are methods for chemical mechanical polishing (CMP) of an object having at least one metal surface. The method comprises contacting the metal surface with a polishing pad; delivering a polishing slurry according to the present disclosure to the metal surface; and polishing said metal surface with the polishing slurry.

In another aspect of the present disclosure, provided herein are methods for preventing metal corrosion during a chemical mechanical polishing (CMP) process. The method comprises using for the CMP a slurry composition according to the present disclosure.

In another aspect of the present disclosure, provided herein are systems for chemical mechanical polishing (CMP). The system comprises a substrate comprising at least one metal surface, a polishing pad, and a polishing slurry according to the present disclosure.

In yet another aspect of the present disclosure, provided herein is a substrate comprising at least one metal surface, wherein the substrate is in contact with a chemical mechanical polishing (CMP) slurry according to the present disclosure.

In some embodiments, the present methods and compositions are suitable for polishing a Co surface. Apparatus or conditions commonly used for Co polishing can be adopted and modified according to particular needs. The selections of suitable apparatus and/or conditions for carrying out the present methods are within the knowledge of a skilled artisan in the art.

In some embodiments, the present methods and compositions provide a corrosion grade of the polished surface of grade 3 or above, according to Table 1. In some embodiments, the present methods and compositions provide a Co removal rate of that is greater than 500 Å/min, or greater than 1000 Å/min, or greater than 1500 Å/min, or greater than 2000 Å/min, or greater than 2500 Å/min, or greater than 3000 Å/min. In some embodiments, the slurry composition of the present methods and compositions produces a Co static etch rate in the range of about 0 to 5 Å/min, or about 5 to about 10 Å/min, or about 10 to about 20 Å/min, or about 20 to about 30 Å/min, or about 30 to about 40 Å/min, or about 40 to about 50 Å/min at 50° C.

EXAMPLES

Example 1: Establishment of a Corrosion Grade System for Evaluating the Corrosion Performance of a Slurry Composition In order to systematically evaluate and compare corrosion performances of candidate slurry compositions, a corrosion grade system is developed as shown in Table 1. Accordingly, for example, a corrosion grade of 1 or above indicates that corrosion on the surface of interest is easily visible to the naked eye of a human inspector, and microscopic inspection using a 10 times (10×) magnification shows that the corrosion affects less than 75% surface area of the surface of interest. For example, a corrosion grade of 4.3 indicates that no corrosion on the surface of interest can be observed with the naked eye of a human inspector, and microscopic inspection using a 10 times (10×) magnification shows that the corrosion affects less than 0.05% surface area of the surface of interest.

TABLE 1

Corrosion grades.

| Grade | Description |
| --- | --- |
| 1 | Corrosion of the surface of interest easily visible with the naked eye. Microscope shows corrosion, affecting <75% surface area of the surface of interest. |
| 2 | Corrosion of the surface of interest visible with the naked eye, and multiple corrosion sizes can be observed. Microscope shows corrosion, affecting <10% surface area of the surface of interest. |
| 3 | Corrosion of the surface of interest not visible to the naked eye. Microscope shows corrosion, affecting <1% surface area of the surface of interest. |
| 4 | Corrosion of the surface of interest not visible with the naked eye. Microscope shows pitting corrosion, affecting <0.05% surface area of the surface of interest. |
| 5 | Very clean, mirror-like surface of interest with no corrosion observable with the naked eye. Microscope proves no corrosion on the surface of interest. |

Acceptable ranges of corrosion grade depend on the particular CMP process and/or requirements of a particular product or manufacturing process, which can be determined with the common skill of the art. In some embodiments, a CMP product having a corrosion grade of 3 or above is considered acceptable.

Example 2: Screening of Candidate Corrosion Inhibitors

In order to find an effective Co corrosion inhibitor, three candidate corrosion inhibitors, namely a lauric acid salt, Capryleth-9 carboxylic acid, and potassium cocoate, were added to a basic slurry composition to the final concentration of 1 mM. In addition to the corrosion inhibitor, the basic slurry composition further contained at least one type of abrasive (e.g., silica), at least one metal complexor (e.g., glycine), and optionally a biocide (e.g., Kathon III). The pH of the composition was adjusted to pH 7.5 (e.g., by adding potassium hydroxide). The compositions of candidate Slurry A, B and C are shown in Table 2.

TABLE 2

Compositions of candidate slurries A, B, and C.

|  | Slurry A | Slurry B | Slurry C |
| --- | --- | --- | --- |
| pH | 7.5 | 7.5 | 7.5 |
| Silica (wt %) | 0.7 | 0.7 | 0.7 |
| KOH (wt %) | 0.009 | 0.009 | 0.009 |
| Glycine (wt %) | 3.65 | 3.65 | 3.65 |
| Lauric acid salt (wt %) | 0.016 | — | — |
| Capryleth-9 carboxylic acid (wt %) | — | 0.086 | — |
| Potassium cocoate (wt %) | — | — | 0.011 |
| Kathon III (wt %) | 0.032 | 0.032 | 0.032 |

Candidate Slurries A, B, and C were tested for their (i) cobalt static etch rates; (ii) Co corrosion grades, and (iii) Co removal rates. Particularly, a Co coupon was immersed within the slurry composition for 3 minutes at 50° C., and the reduction in the thickness of the Co coupon was measured for calculating the static etch rate. Further, the surface of the Co coupon was inspected for corrosion both by the naked eye of a human inspector and with a microscope at 10 times (10×) magnification. Co removal rates were measured. TECHPREP benchtop polisher from Allied High Tech Products, Inc, was used. Platen speed was 250 rpm while head downforce was fixed at 1.06 psi. Head speed was 22 pm. The slurry flow rate was 90 mL/min. Cobalt wafer coupons (1.5"×1.5") were used. Polishing time was 10 sec. Co RR was measured on Resmap. The results were plotted in FIG. 1.

Slurry A produced a Co static etch rate of 47 angstrom per minute (Å/min), a Co corrosion grade of about 1, and a Co removal rate of about 84 Å/min. Slurry B produced a Co static etch rate of 23 Å/min, a Co corrosion grade of about 4.3, and a Co removal rate of about 1736 Å/min. Slurry C produced a Co static etch rate of 36 angstrom per minute (Å/min), a Co corrosion grade of about 1, and a Co removal rate of about 665 Å/min. Thus, capryleth-9 carboxylic acid is a better corrosion inhibitor as compared to lauric acid salt and potassium cocoate, as Slurry B produced significantly better corrosion performance, and maintained a substantially higher Co removal rate, as compared to Slurries A and C.

Example 3: Concentration-Dependent Effects of Candidate Corrosion Inhibitors

Without being bound by the theory, it is contemplated that fatty acids can act as metal corrosion inhibitors because the the carboxylic group (—COOH) of the molecule can attach to the metal surface, while the hydrophobic end of the molecule aligns to form a self-aligned impervious film that inhibits the corrosion. This mechanism of action, however, may cause an undesirable reduction in the metal removal rate during CMP, which would become more prominent as the concentration of the corrosion inhibitor increases.

Figure 2:
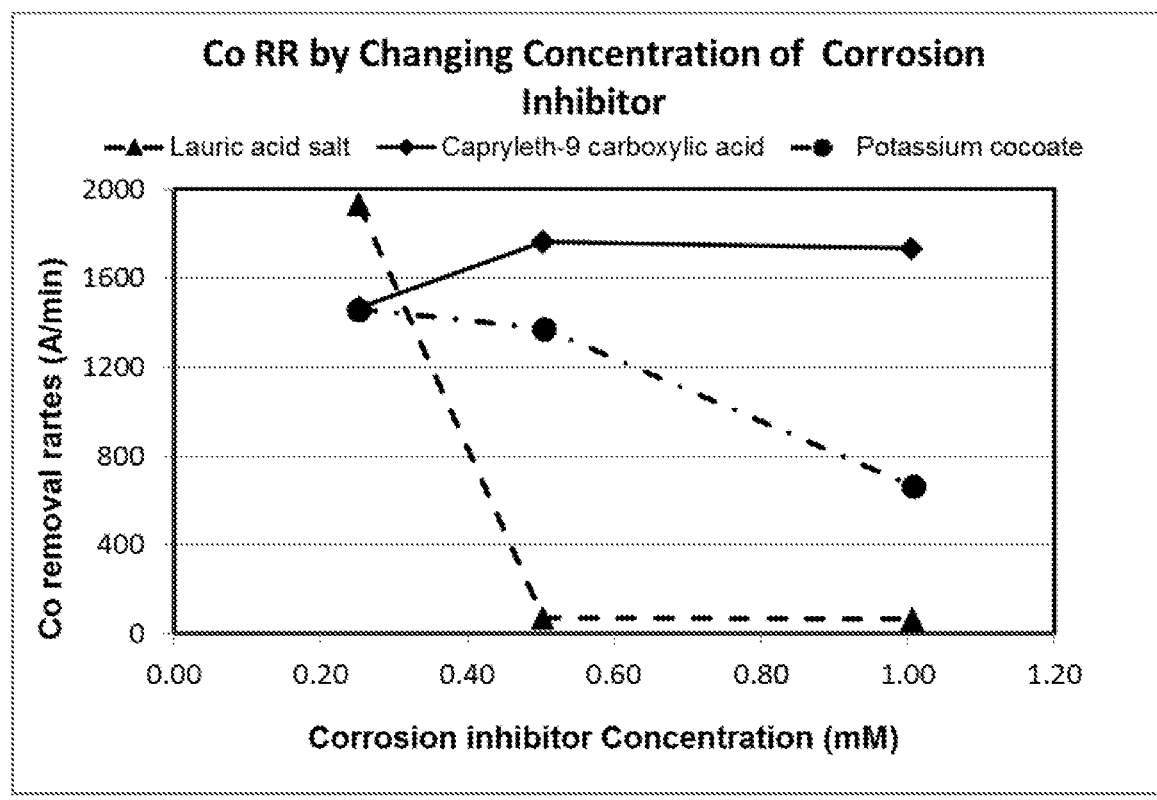
FIG. 2 shows the cobalt removal rates produced by candidate slurries having different corrosion inhibitors at different concentrations.

Thus, the concentration-dependent effect of a candidate corrosion inhibitor on the metal removal rate was examined. Particularly, a candidate corrosion inhibitor was added to the basic slurry composition (as described in Example 2) at concentrations of 0.25 mM, 0.5 mM and 1 mM, respectively. Three candidate corrosion inhibitors, namely a lauric acid salt, capryleth-9 carboxylic acid, and potassium cocoate, were tested. Co removal rates were measured as described in Example 2 for candidate slurries having the different corrosion inhibitors at the varied concentrations. The results were plotted in FIG. 2.

The Co removal rates of slurries A and C decreased with the increase of the concentration of their respective corrosion inhibitor, namely lauric acid salt or potassium cocoate. Surprisingly however, the Co removal rate of slurry B remained substantially stable as the concentration of capryleth-9 carboxylic acid increased.

Figure 3:
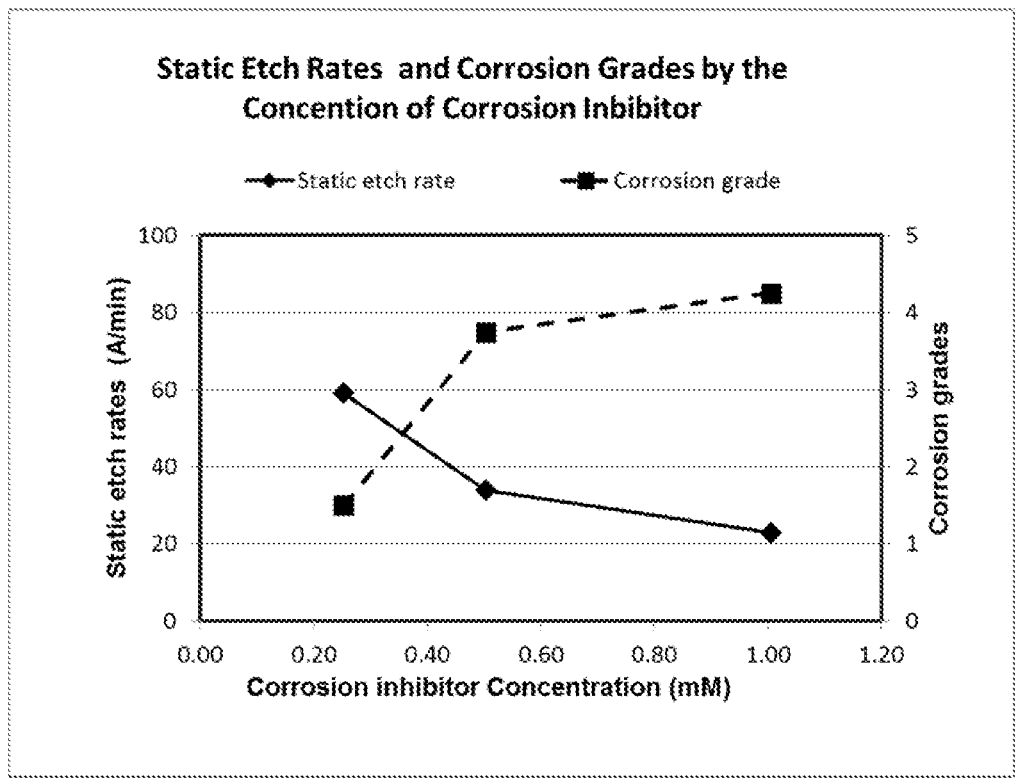
FIG. 3 shows the cobalt static etch rates and corrosion grades produced by candidate slurries having different concentrations of capryleth-9 carboxylic acid.

To further examine the corrosion-inhibiting effect of capryleth-9 carboxylic acid, Co static etching tests were performed with Slurry B containing 0.25 mM, 0.5 mM and 1 mM capryleth-9 carboxylic acid, respectively. Particularly, a Co coupon was immersed within the slurry composition for 3 minutes at 50° C. and the reduction in the thickness of the Co coupon was measured for calculating the static etch rate. Further, the surface of the Co coupon was inspected for corrosion both by the naked eye of a human inspector and with a microscope at 10 times (10×) magnification. The results were plotted in FIG. 3.

As shown, Slurry B exhibited a concentration-dependent effect on inhibiting Co corrosion. Particularly, as the capryleth-9 carboxylic acid concentration increased, the Co static etch rate decreased, resulting in higher corrosion grades. At all concentrations, Slurry B produced acceptable low static etch rates under the harsh testing condition (5 minutes at 50° C.). Consistent with Example 2, the Co static etch rate was about 20 Å/min when the capryleth-9 carboxylic acid concentration reached 1 mM. Slurry B started to produce acceptable corrosion grades when the capryleth-9 carboxylic acid concentration was at least 0.5 mM. Consistent with Example 2, the corrosion grade was about 4.3 when the capryleth-9 carboxylic acid concentration reached 1 mM.

These data indicate that capryleth-9 carboxylic acid exhibits concentration-dependent effects in inhibiting metal corrosion, but does not produce concentration-dependent reduction in the metal removal rate during CMP.

Example 4: Screening of Additional Candidate Corrosion Inhibitors Based on Chemical Structures Capryleth-9 carboxylic acid is a long-chain fatty acid. The chemical structure can be written as:

$$C_mH_{2m+1}-(OCH_2CH_2)_n-OCH_2-COOH$$

where m=n=8;
or alternatively as:

$$R^1-(OCH_2CH_2)_n-OCH_2-COOH$$

where $R^1$ is $C_8$ alkyl; and n=8.

Thus, the capryleth-9 carboxylic acid molecule comprises a hydrophobic end (R), and a carboxylic end (—COOH), with multiple ethylene oxide repeating units —$(CH_2CH_2O)_n$— in between. Without being bound by theory, it is contemplated that the chemical structure of capryleth-9 carboxylic acid enables the compound molecules to form a better protection layer on the metal surface, which, on one hand, offers effective protection against metal corrosion, and on the other hand permits a high metal removal rate during CMP.

Additional candidate compounds having different m and n numbers were screened for their potential as corrosion inhibitors. Particularly, candidate compounds were added to the basic slurry (as described in Example 2) to form candidate slurries D through N as shown in Table 3.

TABLE 3

Compositions of candidate slurries D through N.

| Slurry | Slurry A | Slurry B | Slurry D | Slurry E | Slurry F | Slurry G | Slurry H |
|---|---|---|---|---|---|---|---|
| pH | 7.5 | 7.5 | 7.5 | 7.5 | 7.5 | 7.5 | 7.5 |
| Silica (wt %) | 0.7 | 0.7 | 0.7 | 0.7 | 0.7 | 0.7 | 0.7 |
| KOH (wt %) | 0.009 | 0.009 | 0.009 | 0.009 | 0.009 | 0.009 | 0.009 |
| Glycine (wt %) | 3.65 | 3.65 | 3.65 | 3.65 | 3.65 | 3.65 | 3.65 |
| Kathon III (wt %) | 0.032 | 0.032 | 0.032 | 0.032 | 0.032 | 0.032 | 0.032 |
| Corrosion Inhibitor (%) | Potassium laurate (0.016) | Capryleth-9 carboxylic acid (0.09) | Potassium oleate (0.05) | Capryleth-6 carboxylic acid (0.06) | Laureth-4 carboxylic acid (0.06) | Laureth-11 carboxylic acid (0.14) | Oleth-3 Carboxylic Acid (0.06) |

| Slurry | Slurry I | Slurry J | Slurry K | Slurry L | Slurry M | Slurry N |
|---|---|---|---|---|---|---|
| pH | 7.5 | 7.5 | 7.5 | 7.5 | 7.5 | 7.5 |
| Silica (wt %) | 0.7 | 0.7 | 0.7 | 0.7 | 0.7 | 0.7 |
| KOH (wt %) | 0.009 | 0.009 | 0.009 | 0.009 | 0.009 | 0.009 |
| Glycine (wt %) | 3.65 | 3.65 | 3.65 | 3.65 | 3.65 | 3.65 |
| Kathon III (wt %) | 0.032 | 0.032 | 0.032 | 0.032 | 0.032 | 0.032 |
| Corrosion Inhibitor (%) | Oleth-6 Carboxylic Acid (0.08) | Oleth-10 Carboxylic Acid (0.11) | Capryleth-9 carboxylic acid (0.009) | Oleth-3 Carboxylic Acid (0.014) | Laureth-11 carboxylic acid (0.03) | Laureth-11 carboxylic acid (0.07) |

Co removal rate (Co RR) produced by each candidate slurry was measured TECHPREP benchtop polisher from Allied High Tech Products, Inc, was used for this study. Platen speed was 250 rpm while head downforce was fixed at 1.06 psi. Head speed was 22 pm. The slurry flow rate was 90 mL/min. Cobalt wafer coupons (1.5"×1.5") were used. Polishing time was 10 sec. Co RR was measured on Resmap.

Table 4 summarizes the Co removal rates (Co RR) of screened candidate slurries, and chemical features of the contained corrosion inhibitor candidate compounds, including the number of carbon atoms (m) in the hydrophobic end (R), the number of ethylene oxide repeating units (n), and the molecular weight (MW) of each candidate compound.

TABLE 4

Cobalt removal rates of screened candidate compounds.

| Slurry | pH | Chemical Name | m | n | MW (g/mol) | Co RR (Å/min) |
|---|---|---|---|---|---|---|
| A | 7.5 | Potassium laurate | 12 | 0 | 238 | 67 |
| B | 7.5 | capryleth-9 carboxylic acid | 8 | 8 | 547 | 2199 |
| D | 7.5 | Potassium oleate | 18 | 0 | 320 | 72 |
| E | 7.5 | capryleth-6 carboxylic acid | 8 | 5 | 408 | 134 |
| F | 7.5 | Laureth-4 carboxylic acid | 12-14 | 2.5 | 356 | 57 |
| G | 7.5 | Laureth-11 carboxylic acid | 12-14 | 10 | 907 | 81 |
| H | 7.5 | Oleth-3 carboxylic acid | 16-18 | 2 | 411 | 66 |

TABLE 4-continued

Cobalt removal rates of screened candidate compounds.

| Slurry | pH | Chemical Name | m | n | MW (g/mol) | Co RR (Å/min) |
|---|---|---|---|---|---|---|
| I | 7.5 | Oleth-6 carboxylic acid | 16-18 | 5 | 544 | 69 |
| J | 7.5 | Oleth-10 carboxylic acid | 16-18 | 9 | 720 | 94 |

As shown in Table 4, Slurry B containing capryleth-9 carboxylic acid produced a significantly higher Co removal rate as compared to other screened slurries. This result is highly unexpected, given the structural similarities between capryleth-9 carboxylic acid and some of the screened compounds that showed very poor removal rates.

Figure 4:
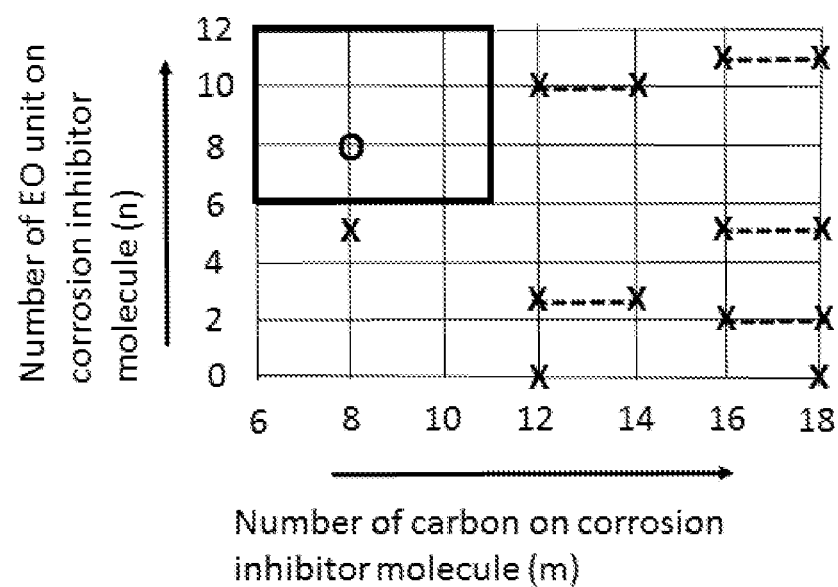
FIG. 4 shows a matrix of the number of carbon atoms (m) in the hydrophobic end (R), and the number of ethylene oxide repeating units (n) of screened corrosion inhibitor candidate compounds.

Without being bound by the theory, it is contemplated that the length of the compound's carbon chain and the length of the hydrophobic end are important for the compound to function as a corrosion inhibitor. A carbon chain that is too long could lead to complete insolubility of the compound in a water-based slurry composition. For example, the compound may tend to form micelles at even low concentrations. A long-chain molecule also tends to wind and twine or agglomerate on the metal surface, leaving unprotected surface or forming a dense protection layer that negatively affects the removal rate. On the other hand, a molecule with too short of a hydrophobic end may not provide sufficient protection against corrosion. FIG. 4 shows the relationship between the number of carbon atoms (m) in the hydrophobic end (R) and the number of ethylene oxide repeating units (n) of screened compounds.

Example 5: Effect of the Carbon Chain Length on the Metal Static Etch Rate

Several candidate slurries as described in above Table 3 were tested for the Co static etch rate (Co SER) with the method described above. The results are summarized in Table 5. As shown, when m is 8 and n is 5, the Co removal rate is low. When m is above 8, regardless whether n is above or below 8, both Co static etch rate and Co removal rate are low. Also molecules with higher critical micelle concentrations (CMC) tends to produce higher Co removal rates and lower Co static etch rates.

TABLE 5

Effect of the carbon chain length (m, n) on cobalt static etch rates.

| Slurry | Chemical Name | m | n | CMC (mg/L) | Co SER (Å/min) | Co RR (Å/min) |
|---|---|---|---|---|---|---|
| E | Capryleth-6 carboxylic acid | 8 | 5 | 102.5 | — | 134 |
| K | Capryleth-9 carboxylic acid | 8 | 8 | 257.8 | 59 | 1940 |
| B | | | | | 23 | 2199 |
| L | Oleth-3 Carboxylic Acid | 16-18 | 2 | 23.2 | 21 | 12 |
| H | | | | | — | 66 |
| M | Laureth-11 Carboxylic Acid | 12-14 | 10 | 41.8 | — | 18 |
| N | | | | | 10 | 12 |

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. It is also to be understood, although not always explicitly stated, that the reagents described herein are merely exemplary and that equivalents of such are known in the art.

All patents, patent applications, provisional applications, and publications referred to or cited herein are incorporated by reference in their entirety, including all figures and tables, to the extent they are not inconsistent with the explicit teachings of this specification.

What is claimed is:

1. A chemical mechanical polishing (CMP) composition comprising at least one abrasive and at least one corrosion inhibitor, wherein the corrosion inhibitor comprises capryleth-9 carboxylic acid having the structure of $CH_3(CH_2)_7(OCH_2CH_2)_8OCH_2COOH$, wherein the abrasive comprises silica particles or alumina particles and is present at a concentration of about 0.01% to 10% by weight, relative to the weight of the composition, and the CMP composition comprises about 0.0001% to about 1% by weight of the corrosion inhibitor.

2. The composition of claim 1, further comprising glycine or a salt thereof.

3. The composition of claim 1, wherein the pH of the composition is in the range of about 6 to about 10, inclusive of the end points.

4. The composition of claim 1, wherein composition produces a cobalt static etching rate of about 20 Å/min or less at 50° C.

5. The composition of claim 1, wherein the composition comprises about 0.1% to about 5% by weight of a complexing agent.

6. The composition of claim 1, wherein the composition comprises an oxidizing agent.

7. The composition of claim 1, wherein the abrasive has a mean particle size of between 0.01 and 0.30 micron.

8. A method for chemical mechanical polishing (CMP) of an object having at least one metal surface, comprising:
contacting the metal surface with a polishing pad;
delivering a polishing slurry to the metal surface,
wherein the polishing slurry comprises at least one abrasive and at least one corrosion inhibitor;
wherein the abrasive comprises silica particles or alumina particles and is present at a concentration of about 0.01% to 10% by weight, relative to the weight of the composition; and
wherein the corrosion inhibitor is present at a concentration of about 0.0001% to about 1% by weight, relative to the total weight of the composition, and comprises capryleth-9 carboxylic acid having the structure of $CH_3(CH_2)_7(OCH_2CH_2)_8OCH_2COOH$; and
polishing the metal surface with the polishing slurry.

9. The method of claim 8, wherein metal is cobalt (Co).

10. The method of claim 8, wherein the method is capable of achieving at least Grade 3 corrosion grade at a Co removal rate of greater than 2000 Å/min.

11. The method of claim 8, wherein the method produces a polished surface devoid of corrosion visible to the naked eye.

12. The method of claim 8, wherein the method produces a polished surface comprising total corrosion area observable under 10×magnification of a microscope of less than 1% of the total area of the polished surface.

13. A system for chemical mechanical polishing (CMP) comprising a substrate comprising at least one metal surface; a polishing pad, and a polishing slurry,
wherein the polishing slurry comprises at least one abrasive and at least one corrosion inhibitor;
wherein the abrasive comprises silica particles or alumina particles and is present at a concentration of about 0.01% to 10% by weight, relative to the weight of the composition; and
wherein the corrosion inhibitor is present at a concentration of about 0.0001% to about 1% by weight, relative to the total weight of the composition and comprises capryleth-9 carboxylic acid having the structure of $CH_3(CH_2)_7(OCH_2CH_2)_8OCH_2COOH$.

* * * * *